United States Patent [19]

Ray

[11] Patent Number: 4,800,875
[45] Date of Patent: Jan. 31, 1989

[54] SURGICAL FUNNEL AND METHOD OF USING

[75] Inventor: Charles D. Ray, Deephaven, Minn.

[73] Assignee: Cedar Surgical, Inc., Minnetonka, Minn.

[21] Appl. No.: 87,423

[22] Filed: Aug. 20, 1987

[51] Int. Cl.$^4$ .................. A61F 5/04; B67C 11/02
[52] U.S. Cl. ................ 128/92 V; 128/303 R; 193/2 R; 141/331
[58] Field of Search ........... 128/92 V, 92 VP, 303 R, 128/92 R; 604/277, 332, 334, 356, 357; 193/2 R; D7/37, 68, 104; 294/55; 141/98, 108, 109, 311, 331, 333, 334, 337, 339–342, 358, 328

[56] References Cited

U.S. PATENT DOCUMENTS

| | | | |
|---|---|---|---|
| 145,720 | 12/1873 | Chess | 193/2 R |
| D. 248,078 | 6/1978 | Warnekros | 141/98 |
| D. 266,301 | 9/1982 | Hall | D7/37 |
| 636,735 | 11/1899 | Davenport | 294/55 |
| 952,313 | 3/1910 | Droz | 141/334 |
| 2,411,384 | 11/1946 | Miller et al. | 141/331 |
| 3,255,570 | 6/1966 | Weimer | 141/108 |
| 4,494,581 | 1/1985 | Gordon | 141/331 |

FOREIGN PATENT DOCUMENTS

| | | | |
|---|---|---|---|
| 811018 | 7/1949 | Fed. Rep. of Germany | 294/55 |
| 2159129 | 11/1985 | United Kingdom | 141/331 |

*Primary Examiner*—Stephen C. Pellegrino
*Assistant Examiner*—Ralph Lewis
*Attorney, Agent, or Firm*—Moore & Hansen

[57] ABSTRACT

Particulate bone is more easily and quickly guided into position for impaction into the site of a fusion mass by using a surgical funnel provided by an elongated, thin, flat base and a pair of thin, upstanding walls which extend along the elongated edges of the base to provide a chute. While the outlet of the funnel rests against the recipient site, particulate bond is incrementally pushed from the chute and tamped to build a fushion mass. By doing so, the particulate bone is much less likely to become contaminated by soft tissues. Preferably the reservoir provided by the upstanding walls is large enough to hold sufficient particulate bond to complete one side of a usual fusion mass so that the funnel can be left in position during that part of the surgical procedure. The funnel can be a single piece of metal or plastic.

17 Claims, 1 Drawing Sheet

SURGICAL FUNNEL AND METHOD OF USING

BACKGROUND ART

1. Field of the Invention

The invention concerns a surgical procedure which uses a funnel for guiding particulate bone into position for impaction into the site of a fusion mass. The novel surgical procedure is especially useful for posterior or posterolateral intertransverse process spinal fusions. The invention also concerns a surgical funnel that can be used in the novel surgical procedure.

2. Description of Related Art

It is common to perform a fusion by impacting particulate bone, typically consisting of a mixture of both cancellous and cortical bone pieces plus blood clots. The usual procedure involves retracting tissue away from the site to be reconstructed, preparting the recipient site, dumping the particulate bone a little at a time onto the site, and then impacting the particulate bone with a bone tamper. The dumping usually is done with a small spatula or spoon, usually somewhat haphazardly because it is difficult to direct the particulate bone with any sort of precision. If the particulate bone is not confined to the recipient site, it tends to become contaminated by soft tissues while being pushed into position, and this may ultimately result in segmentation of the fusion. After the particulate bone has been tamped into place, the fusion may be covered with an oxidized cellulosic gauze which remains in place, thus adding fibrous tissue to the particulate bone.

SUMMARY OF THE INVENTION

The invention provides a surgical procedure for guiding particulate bone into position for impaction into the site of a fusion mass, which procedure is faster and more convenient than prior procedures. Furthermore, in the novel surgical procedure, the particulate bone is much less likely to become contaminated by soft tissues when being positioned for impaction into the site of a fusion mass. Briefly, the novel surgical procedure involves the steps of (1) loading particulate bone into an open reservoir of a surgical funnel provided by an elongated, thin, flat base and a pair of thin, upstanding walls which extend along the elongated edges of the base to provide a chute, (2) resting the outlet of the funnel against the recipient site, (3) pushing the loaded particulate bone from the chute to deposit increments of the particulate bone onto the prepared site, and while leaving the funnel in place, (4) tamping each deposited increment to build a fusion mass incrementally.

In carrying out the novel surgical procedure, it has been found to be convenient after tamping a deposited increment to employ a suction tube to keep the fusion mass relatively dry before depositing another increment. This is easily accomplished without shifting the position of the outlet of the funnel or disturbing the remainder of the loaded particulate bone. Care should be taken in step (3) so that each deposited increment remains within the cross-sectional area of the chute at its outlet and so does not become contaminated.

A funnel which is particularly useful in the novel surgical procedure has
an elongated, thin, flat base,
a pair of thin, upstanding walls extending along the elongated edges of the base to form an open reservoir which can be filled with particulate bone and includes a chute of substantially uniform width that is unobstructed at one end to provide an outlet for the particulate bone,
the base and upstanding walls gradually extending outwardly beyond the other (inlet) end of the chute to provide an expanded reservoir,
the upstanding walls tapering from the outlet to a significantly greater height at the other end of the base,
the extremities of both the base and the upstanding walls at the outlet being blunt to enhance lateral movement of the funnel within a surgical wound, and
a handle at said other end of the base.

The handle should extend in the direction opposite to the upstanding walls so that the surgeon's hand will not obstruct his or her vision.

The chute of the novel funnel should be of substantially uniform width to permit the surgical incision to be small while allowing a tamping instrument of reasonably large size to fit easily between the upstanding walls. Beyond the inlet or throat of the chute, the upstanding walls gradually extend outwardly to provide a usefully large reservoir. A deviation from 20°–40° should be adequate without causing any awkwardness.

Preferably the width of the chute at its outlet approximates the length of the gap between bony elements to be fused, thereby minimizing the need to move the chute laterally as the tamping proceeds. For use in the lumbar area, a width from 1.0 to 3.0 cm should be useful. The extremities of both the base and the upstanding walls at the outlet should be blunt, preferably rounded, to enhance lateral movement of the funnel within a surgical wound.

Preferably the reservoir is of a size that holds enough particulate bone necessary for one side of a usual fusion mass so that the funnel can be left in position during that part of the surgical procedure. On the other hand, the upstanding walls should be low at the outlet so that the surgical wound can be quite small, and yet the walls should be high enough to permit the deposited increments of particulate bone to be of useful size. A height at the outlet of from 0.3 to 0.7 cm is preferred for use in the lumbar area. Lesser heights might permit the particulate bone to fall out of the side of the chute. Greater heights would require greater retraction and hence more exposure. The upstanding walls should taper uniformly from one end of the base to the other, preferably reaching a height such that the reservoir can hold 2 ounces (60 grams) of particulate bone, enough to complete one side of a fusion mass of the lumbar area. Wall heights from 0.8 to 3.0 cm at the inlet of the chute should be useful. For use in the lumbar area, the length of the chute should be from 8 to 12 cm.

For use in the cervical spine area, the novel funnel can be somewhat smaller and lighter, but a funnel esigned for use in the lumbar area can also be used in the cervical spine area.

The base, upstanding walls, and handle of the novel surgical funnel preferably are shaped from a single piece of metal or plastic. When metal, it should withstand repeated sterilization such as stainless steel. When plastic, it should be sufficiently inexpensive to be discarded after each use, e.g., injection molded polypropylene. Whether plastic or metal, the base and walls of the novel funnel should be of uniform thickness and sufficiently thin so that the funnel is light in weight and easy to use, e.g., from 0.5 to 1.0 mm in thickness when metal or from 1.0 to 1.5 mm when plastic.

THE DRAWING

In the drawing, all figures of which are schematic,

Figure 1:
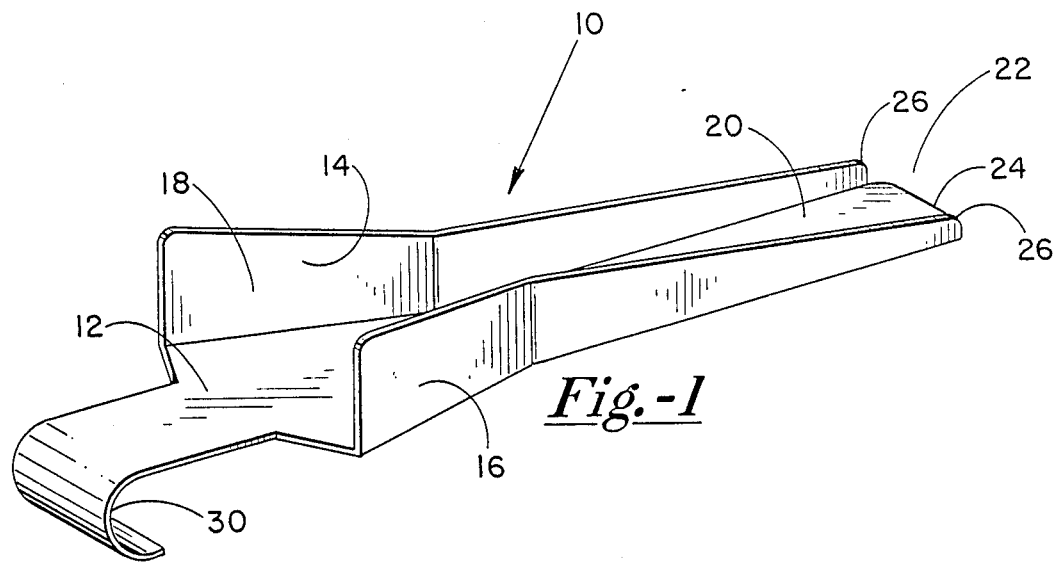
FIG. 1 is an isometric view of a preferred surgical funnel of the invention.
Figure 2:
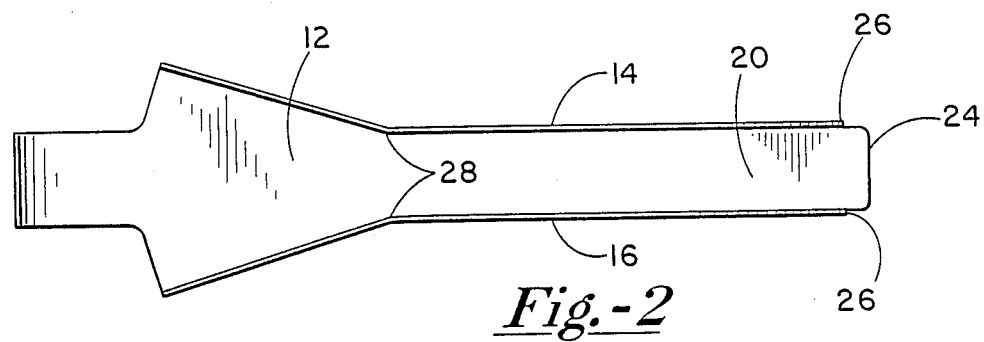
FIG. 2 is a plan view of the funnel shown in FIG. 1.
Figure 3:
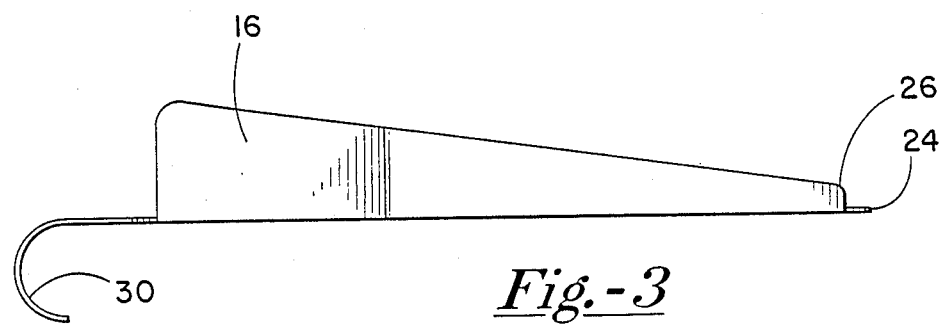
FIG. 3 is an elevation of the funnel shown in FIGS. 1 and 2.

The illustrated surgical funnel 10 has an elongated, thin, flat base 12 and a pair of thin, upstanding walls 14 and 16 extending along the elongated edges of the base to form an open reservoir 18 including a chute 20 of a substantially uniform width of about 2 cm and a length of about 10 cm. The chute is unobstructed at one end of the base 12 to provide an outlet 22 for particulate bone. The base at the outlet 22 is rounded at its extremity 24, and the adjacent extremities 26 of the walls 14,16 are also rounded to enhance lateral movement of the funnel when it is inserted into a surgical wound, each round having a radius of about 5 mm.

At the other end or inlet of the chute 20, the reservoir 18 has a throat 28, beyond which each of the upstanding walls 14,16 is deflected outwardly at an angle of about 30° from the walls of the chute, thus expanding the area of the reservoir. Each of the walls 14,16 tapers uniformly from a height of about 0.5 cm at the outlet 22 of the chute to about 2.5 cm at its other extremity at which the base 12 curves away from the walls 14,16 to form a semi-cylindrical handle 30 having a radius of about one cm.

The illustrated surgical funnel 10 has been constructed by shaping a piece of 303 stainless steel having a thickness of about 0.75 mm. It has been used in posterior or posterolateral intertransverse process spinal fusions without any contamination of the particulate bone, and its use has made the fusion process both faster and easier to perform. In doing so, the tamping instrument that has been most useful is the surgical impactor shown in FIG. 7 of U.S. Pat. No. 4,657,002 (Ray).

I claim:

1. Method of guiding particulate bone to a properly prepared recipient site and for impacting the particualte bone into a fusion mass, said method comprising the steps of (1) loading the particulate bone into an open reservoir of a surgical funnel provided by an elongated, thin, flat base and a pair of thin, upstanding walls which extend along the elongated edges of the base to provide a chute, (2) resting the outlet of the funnel against the recipient site, (3) pushing increments of the loaded particulate bone from the chute onto the prepared site, and while leaving the funnel in place, (4) tamping each deposited increment to build a fusion mass incrementally.

2. Method as defined in claim 1 wherein the amount of particulate bone which is loaded into the reservoir in step (1) is sufficient to complete one side of a usual fusion mass so that the funnel can be lest in position during that part of the surgical procedure.

3. Method as defined in claim 2 wherein each increment of particulate bone is deposited in step (3) to remain within the cross-sectional area of the chute at its outlet.

4. A surgical funnel useful for guiding particulate bone into position for impaction and comprising:

an elongated, thin, flat base, a pair of thin, upstanding walls extending along and terminating at the ends of the elongated edges of the base to form an open reservoir including a chute of substantially uniform width which has an inlet and an outlet, both unobstructed, the base and upstanding walls gradually extending outwardly beyond the other end of the chute to provide an expanded reservoir, the upstanding walls being rounded at the outlet and tapering from the outlet to a significantly greater height at the other end of the base, the base at the outlet of the chute extending beyond the upstanding walls and being rounded to enhance lateral movement of the funnel within a surgical wound, and a handle at said other end of the base curving away from the base and the upstanding walls.

5. A surgical funnel as defined in claim 4 wherein the width of the outlet of the funnel approximates the length of the gap between bony elements to be fused, thereby minimizing the need to move the chute laterally.

6. A surgical funnel as defined in claim 5 wherein the chute is from one to 3 cm in width.

7. A surgical funnel as defined in claim 6 wherein the chute is from 8 to 12 cm in length.

8. A surgical funnel as defined in claim 7 wherein the height of the walls is from 0.3 to 0.7 cm at the outlet of the chute.

9. A surgical funnel as defined in claim 8 wherein the walls taper uniformly from the outlet to the inlet of the chute, and the height of the walls at the inlet is from 0.8 to 3.0 cm.

10. A surgical funnel as defined in claim 4 wherein each of the walls extends outwardly beyond said other end of the chute at an angle of 20°–40° from the walls along the chute.

11. A surgical funnel as defined in claim 4 wherein the size of the reservoir is sufficient to hold 2 ounces of particulate bone.

12. A surgical funnel as defined in claim 4 wherein handle is an extension of the base and curves away from base and the upstanding walls in a C-shaped configuration.

13. A surgical funnel as defined in claim 4 wherein the base, upstanding walls, and handle are shaped from a piece of metal.

14. A surgical funnel as defined in claim 13 wherein the metal is stainless steel, and the base and upstanding walls are of uniform thickness between 0.5 and 1.0 mm.

15. A surgical funnel as defined in claim 4 wherein the base, upstanding walls, and handle are a single piece of plastic.

16. A surgical funnel as defined in claim 15 wherein the plastic is injection molded polypropylene, and the base and upstanding walls are of uniform thickness between 1.0 and 1.5 mm.

17. A surgical funnel formed from a single piece of metal or plastic or uniform thickness and useful for guiding particulate bone into position for impaction and consisting of an elongated flat base, a pair of upstanding walls extending along and terminating at the ends of the elongated edges of the base to form an open reservoir including a chute of substantially uniform width of about 2 cm, which chute has an inlet and an outlet, both unobstructed, each of the base and upstanding walls gradually extending outwardly beyond the inlet end of the chute at an angle of 20°-40° to the walls along the chute, thus providing an expanded reservoir, the upstanding walls tapering uniformly from a height of about 0.5 cm adjacent the outlet to about 2.5 cm at the other end of the base, the extremities of both the base and the upstanding walls at the outlet being rounded to enhance lateral movement of the funnel within a surgical wound, and a handle at said other end of the base curving away from the base and the upstanding walls to form a semi-cylinder having a radius of about one cm.

* * * * *

UNITED STATES PATENT AND TRADEMARK OFFICE
CERTIFICATE OF CORRECTION

PATENT NO. : 4,800,875
DATED : January 31, 1989
INVENTOR(S) : Charles D. Ray

It is certified that error appears in the above-identified patent and that said Letters Patent is hereby corrected as shown below:

In column 1, line 18, after reconstructed, change "preparting" to --preparing--.

In claim 17, column 4, line 62, after "metal or plastic", change "or" to --of--.

Signed and Sealed this

Fourteenth Day of November, 1989

Attest:

JEFFREY M. SAMUELS

*Attesting Officer*   *Acting Commissioner of Patents and Trademarks*